United States Patent
Huang et al.

(10) Patent No.: US 8,255,178 B2
(45) Date of Patent: Aug. 28, 2012

(54) METHOD FOR DETECTING STATUSES OF COMPONENTS OF SEMICONDUCTOR EQUIPMENT AND ASSOCIATED APPARATUS

(75) Inventors: Yu-Chang Huang, Taipei County (TW); Chia-Wei Fan, Taoyuan (TW)

(73) Assignee: Inotera Memories, Inc., Hwa-Ya Technology Park Kueishan, Taoyuan (TW)

( * ) Notice: Subject to any disclaimer, the term of this patent is extended or adjusted under 35 U.S.C. 154(b) by 355 days.

(21) Appl. No.: 12/652,733

(22) Filed: Jan. 5, 2010

(65) Prior Publication Data
US 2011/0106499 A1 May 5, 2011

(30) Foreign Application Priority Data
Nov. 3, 2009 (TW) .............................. 98137232 A

(51) Int. Cl.
*G06F 15/00* (2006.01)
*G01R 23/00* (2006.01)

(52) U.S. Cl. ........... 702/75; 702/184; 704/205; 704/249
(58) Field of Classification Search .................... 702/75, 702/184, 188; 704/205, 249, 254, 231, 270, 704/274
See application file for complete search history.

(56) References Cited

U.S. PATENT DOCUMENTS
| | | | |
|---|---|---|---|
| 6,996,527 B2* | 2/2006 | Boman et al. ................ | 704/239 |
| 2002/0035447 A1* | 3/2002 | Takahashi et al. ............ | 702/188 |
| 2008/0082323 A1* | 4/2008 | Bai et al. ...................... | 704/214 |

* cited by examiner

*Primary Examiner* — Sujoy Kundu
(74) *Attorney, Agent, or Firm* — Winston Hsu; Scott Margo

(57) ABSTRACT

An apparatus for detecting an operational status of a semiconductor equipment includes an audio frequency signal receiving unit and an analysis and determination unit. The audio frequency signal receiving unit is used for receiving an audio frequency signal from the semiconductor equipment while the semiconductor equipment is working. The analysis and determination unit is used for analyzing the audio frequency signal to determine statuses of components of the semiconductor equipment.

18 Claims, 3 Drawing Sheets

METHOD FOR DETECTING STATUSES OF COMPONENTS OF SEMICONDUCTOR EQUIPMENT AND ASSOCIATED APPARATUS

BACKGROUND OF THE INVENTION

1. Field of the Invention

The present invention relates to a method for detecting an operational status of a semiconductor equipment, and more particularly, to a method for detecting statuses of components of a semiconductor equipment according to an audio frequency signal generated from the semiconductor equipment while the semiconductor equipment is working, and an associated apparatus.

2. Description of the Prior Art

With a long term operation of a semiconductor equipment, components of the semiconductor equipment will suffer from aging or wear. Therefore, to prevent wafers from being damaged due to the aged or worn components, an engineer uses special tools to check the statuses of the components of the semiconductor equipment. Furthermore, the engineer can also check these statuses by visual inspection or listening to the sound generated from the semiconductor equipment.

However, because each person has a unique sensation while listening to the same audio frequency, when the engineer listens to the sound generated from the semiconductor equipment to determine the statuses of the components, each engineer checks the statuses of the components according to his experience, which means the determinations are not objective. In addition, humans generally have less sensitivity to sounds having a frequency greater than 1 kHz, so the engineer may not truly determine whether components are aged or worn.

SUMMARY OF THE INVENTION

It is therefore an objective of the present invention to provide a method for detecting an operational status of a semiconductor equipment according to an audio frequency signal from the semiconductor equipment, and an associated apparatus, to solve the above-mentioned problems.

According to one embodiment of the present invention, a method for detecting an operational status of a semiconductor equipment comprises: receiving an audio frequency signal from the semiconductor equipment while the semiconductor equipment is working; and analyzing the audio frequency signal to determine statuses of components of the semiconductor equipment.

According to another embodiment of the present invention, an apparatus for detecting an operational status of a semiconductor equipment comprises an audio frequency signal receiving unit and an analysis and determination unit. The audio frequency signal receiving unit is used for receiving an audio frequency signal from the semiconductor equipment while the semiconductor equipment is working. The analysis and determination unit is used for analyzing the audio frequency signal to determine statuses of components of the semiconductor equipment.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
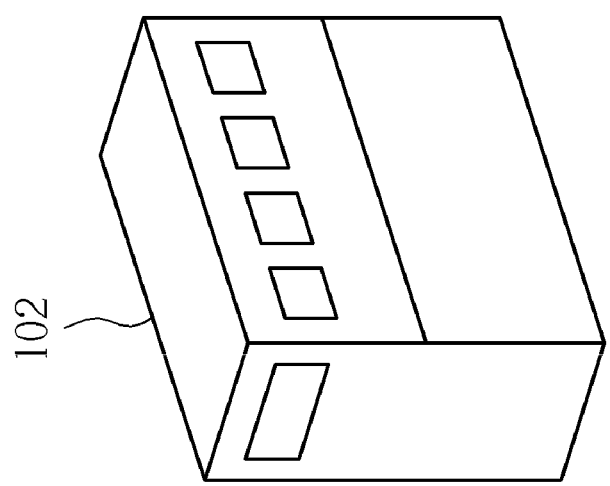
FIG. 1 is a diagram illustrating an apparatus, which is used for detecting an operational status of a semiconductor equipment, according to one embodiment of the present invention.
Figure 1:
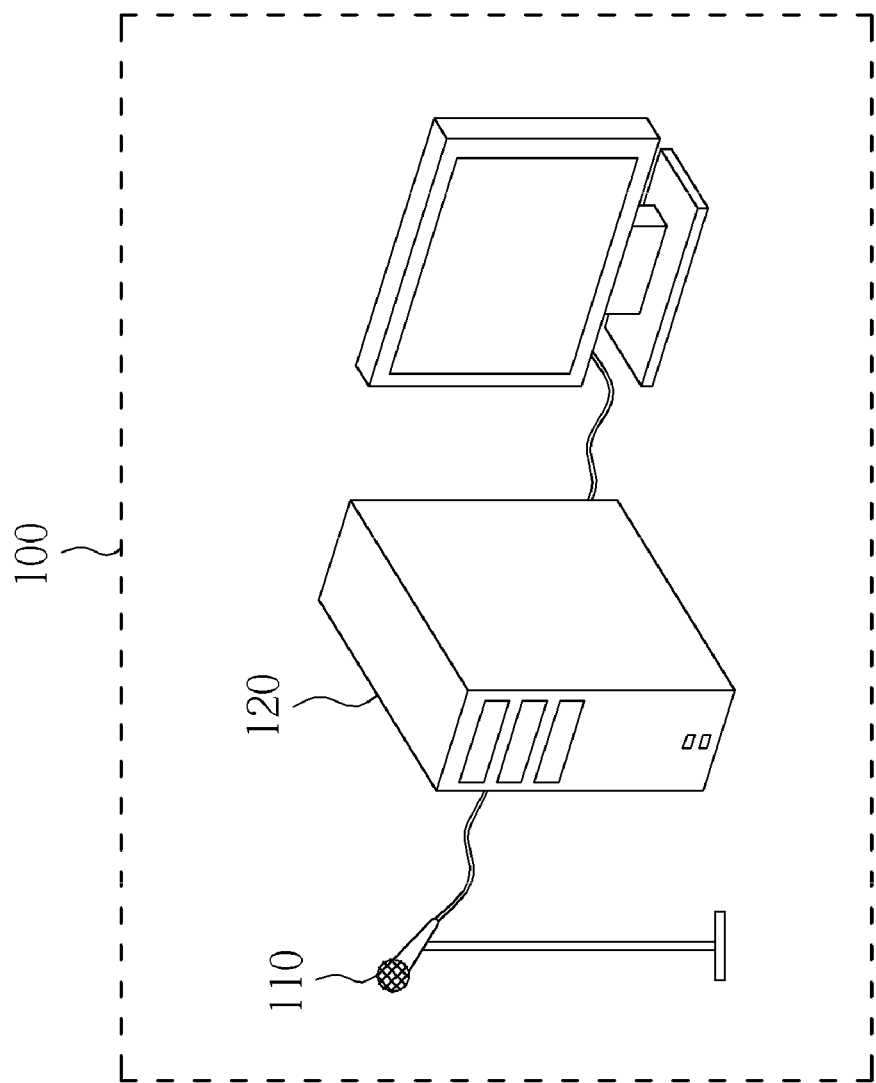

Please refer to FIG. 1. FIG. 1 is a diagram illustrating an apparatus 100, which is used for detecting an operational status of a semiconductor equipment, according to one embodiment of the present invention. As shown in FIG. 1, the apparatus 100 includes an audio frequency signal receiving unit 110 and an analysis and determination unit (in this embodiment the analysis and determination unit is implemented by a computer 120, which has an audio frequency collection and analysis function and a database). The audio frequency signal receiving unit 110 is positioned next to a semiconductor equipment 102 to make the audio frequency signal receiving unit 110 able to receive the audio frequency signal generated from the semiconductor equipment 102 while the semiconductor equipment 102 is working. In addition, in one embodiment of the present invention, the semiconductor equipment 102 can be a coater and developer.

Figure 2A:
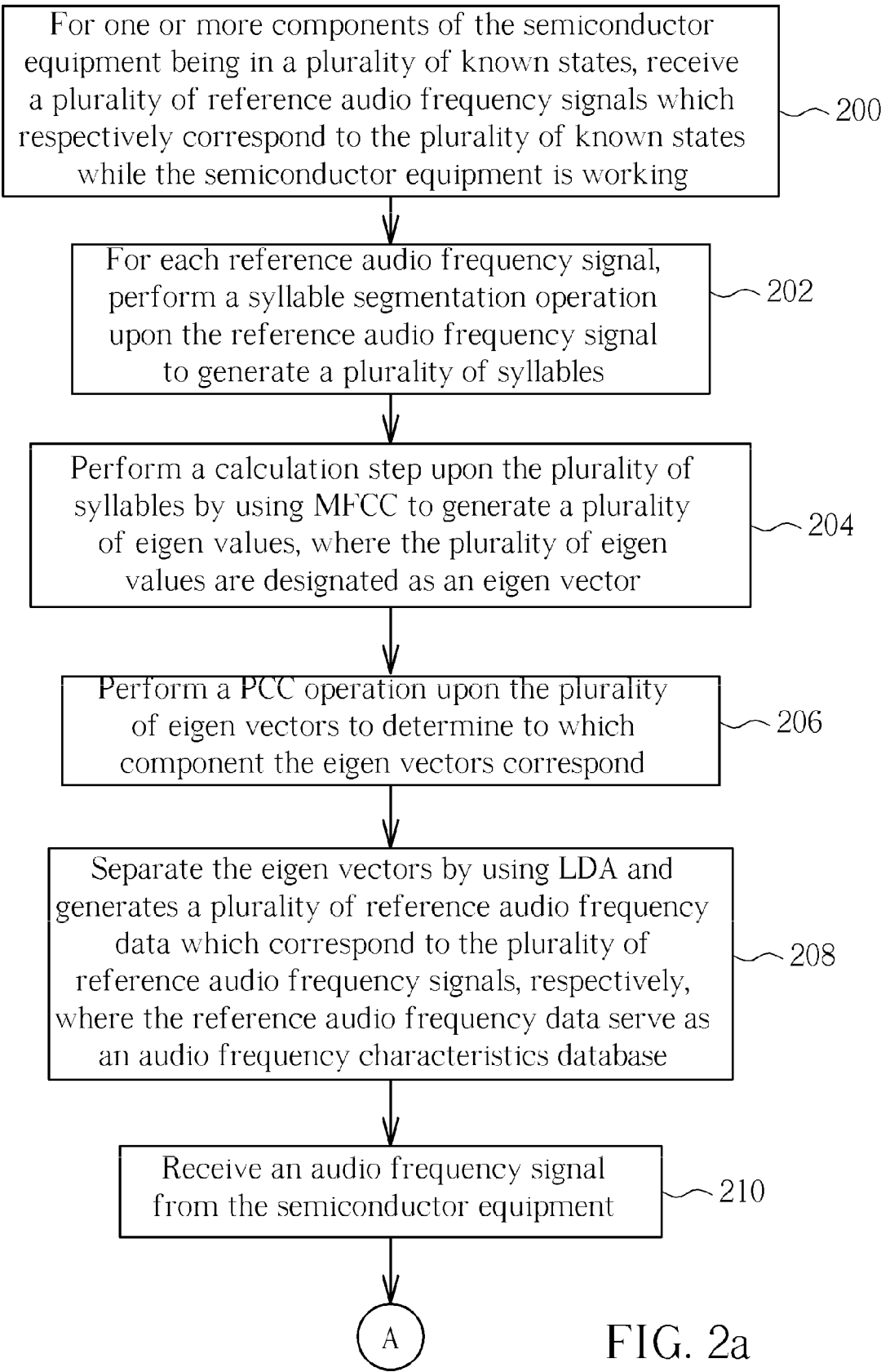
FIGS. 2a and 2b are flow charts of a method for detecting an operational status of the semiconductor equipment according to one embodiment of the present invention.
Figure 2B:
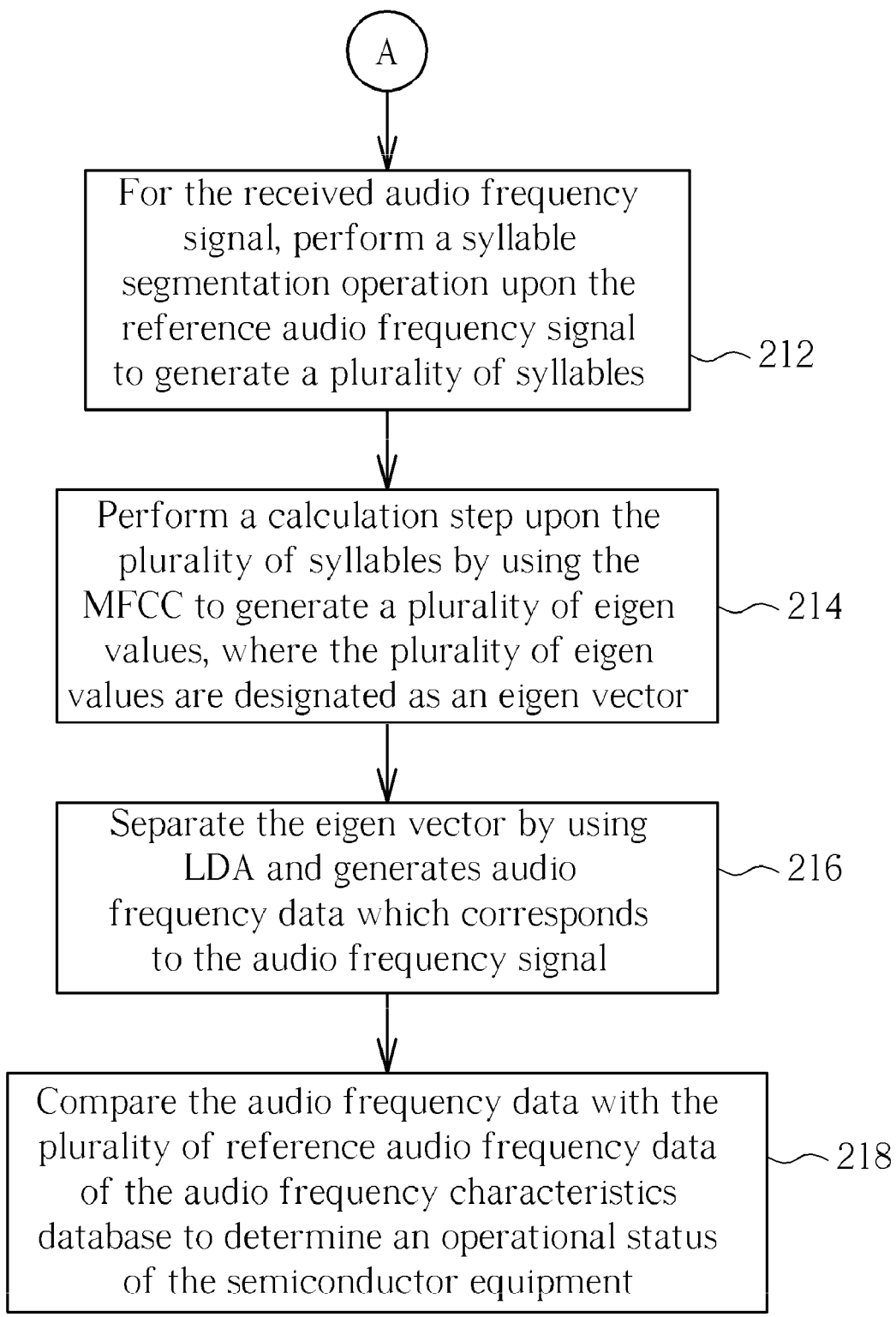

Please refer to FIG. 2, FIG. 2a and FIG. 2b together. FIGS. 2a and 2b are flow charts of a method for detecting an operational status of the semiconductor equipment 102 according to one embodiment of the present invention. Please note that, provided that the results are substantially the same, the steps are not limited to be executed according to the exact order shown in FIGS. 2a and 2b Referring to FIGS. 2a, 2b, the flow is described as follows:

First, in Step 200, for one or more components of the semiconductor equipment 102 being in a plurality of known states, the audio frequency signal receiving unit 110 receives a plurality of reference audio frequency signals which respectively correspond to the plurality of known states while the semiconductor equipment 102 is working, and the audio frequency signal receiving unit 110 transmits the received reference audio frequency signals to the computer 120. For example, the audio frequency signal receiving unit 110 can receive a plurality of audio frequency signals generated from the semiconductor equipment 102 when a belt is at different aging states, respectively; and the audio frequency signal receiving unit 110 can also receive a plurality of audio frequency signals generated from the semiconductor equipment 102 when a component of a motor is at different wear degrees, respectively. The received audio frequency signals serve as the reference audio frequency signals, and are transmitted to the computer 120.

In Step 202, for each reference audio frequency signal, a computer program of the computer 120 performs a syllable segmentation operation upon the reference audio frequency signal to generate a plurality of syllables. In Step 204, the computer program performs a calculation step upon the plurality of syllables by using mel-frequency cepstrum coefficients (MFCC) to generate a plurality of eigen values (i.e., mel-scale frequency cepstral analysis), where the plurality of eigen values are designated as an eigen vector. In other words, the computer program generates a plurality of eigen vectors which correspond to the plurality of audio frequency signals, respectively. For example, a first eigen vector corresponds to an audio frequency generated from the belt which is at a normal state, and a second eigen vector corresponds to an audio frequency generated from the belt which is at an aging state etc.

In addition, when the semiconductor equipment 102 is working, many components of the semiconductor equipment 102 will make sounds at the same time. Therefore, to identify the plurality of eigen vectors generated in Step 204, in Step 206, the computer program performs a progressive constructive clusters (PCC) operation upon the plurality of eigen vectors to determine to which component the eigen vectors correspond.

In Step 208, the computer program separates the eigen vectors by using a linear discrimination analysis (LDA) and generates a plurality of reference audio frequency data which correspond to the plurality of reference audio frequency signals, respectively. The computer program further stores the reference audio frequency data into a storage device (not shown) of the computer 120, where the reference audio frequency data serve as an audio frequency characteristics database.

Briefly summarized, Steps 202-208 are for building audio frequency characteristics database according to the reference audio frequency signals generated from the semiconductor equipment 102 while the semiconductor equipment 102 is working, where the audio frequency signals correspond to the plurality of known states of one or more components of the semiconductor equipment 102.

In Step 210, the semiconductor equipment 102 starts manufacturing, and the audio frequency signal receiving unit 110 receives an audio frequency signal from the semiconductor equipment 102, and transmits the audio frequency signal to the computer 120.

In Step 212, for the received audio frequency signal, the computer program of the computer 120 performs a syllable segmentation operation upon the reference audio frequency signal to generate a plurality of syllables. Then, in Step 214, the computer program performs a calculation step upon the plurality of syllables by using the mel-frequency cepstrum coefficients (MFCC) to generate a plurality of eigen values, where the plurality of eigen values are designated as an eigen vector.

In Step 216, the computer program separates the eigen vector by using linear discrimination analysis (LDA) and generates audio frequency data which corresponds to the audio frequency signal. Then, in Step 218, the computer program compares the audio frequency data with the plurality of reference audio frequency data of the audio frequency characteristics database to determine an operational status of the semiconductor equipment 102, and to further determine which component is at an abnormal state and needs replacing, or to determine which component is in an alarm state and requires maintenance.

Briefly summarizing the method for detecting an operational status of the semiconductor equipment and associated apparatus of the present invention: first, an audio frequency characteristics database is built according to reference audio frequency signals generated from the semiconductor equipment while the semiconductor equipment is working, the components of the semiconductor equipment being in a plurality of states. Then, when the semiconductor equipment starts manufacturing, the audio frequency signal generated from the semiconductor equipment is received and analyzed to generate an audio frequency data, and the audio frequency data is compared with the data of the audio frequency characteristics database to determine an operational status of the semiconductor equipment. Therefore, the aged or worn status of the components of the semiconductor equipment can be determined based on an objective standard.

Those skilled in the art will readily observe that numerous modifications and alterations of the device and method may be made while retaining the teachings of the invention.

What is claimed is:

1. A method for detecting an operational status of a semiconductor equipment, comprising:
    receiving an audio frequency signal generated from the semiconductor equipment while the semiconductor equipment is working; and
    analyzing the audio frequency signal to determine statuses of components of the semiconductor equipment.

2. The method of claim 1, wherein the step of analyzing the audio frequency signal comprises:
    analyzing the audio frequency signal by utilizing a mel-scale frequency cepstral analysis to determine the statuses of the components of the semiconductor equipment.

3. The method of claim 1, wherein the step of analyzing the audio frequency signal comprises:
    analyzing the audio frequency signal to generate an audio frequency data; and
    comparing the audio frequency data with a plurality of reference audio frequency data of an audio frequency characteristics database to determine the statuses of the components of the semiconductor equipment.

4. The method of claim 3, further comprising:
    for one or more component of the semiconductor equipment at a plurality of known states, receiving a plurality of reference audio frequency signals generated from the semiconductor equipment while the semiconductor equipment is working;
    analyzing the plurality of reference audio frequency signals to generate a plurality of reference audio frequency data; and
    building the audio frequency characteristics database according to the plurality of reference audio frequency data.

5. The method of claim 4, wherein the step of analyzing the plurality of reference audio frequency signals to generate the plurality of reference audio frequency data comprises:
    for each reference audio frequency signal:
        performing a syllable segmentation operation upon the reference audio frequency signal to generate a plurality of syllables;
        performing a calculation step upon the plurality of syllables by using mel-frequency cepstrum coefficients to generate a plurality of eigen values, where the plurality of eigen values are designated as an eigen vector; and
        generating a reference audio frequency data which corresponds to the reference audio frequency signal according to the eigen vector.

6. The method of claim 5, wherein the step of generating the reference audio frequency data which corresponds to the reference audio frequency signal according to the eigen vector comprises:
    utilizing a linear discrimination analysis to separate the eigen vector and other eigen vectors to generate the reference audio frequency data which correspond to the reference audio frequency signal.

7. The method of claim 1, wherein the step of analyzing the audio frequency signal to determine the statuses of the components of the semiconductor equipment comprises:
    determining which component of the semiconductor equipment is in an abnormal state and requires replacing.

8. The method of claim 1, wherein the step of analyzing the audio frequency signal to determine the statuses of the components of the semiconductor equipment comprises:
    determining which component of the semiconductor equipment is in an alarm state and requires maintenance.

9. The method of claim 1, wherein the semiconductor equipment is a coater and developer.

10. An apparatus for detecting an operational status of a semiconductor equipment, comprising:
  an audio frequency signal receiving unit, for receiving an audio frequency signal generated from the semiconductor equipment while the semiconductor equipment is working; and
  an analysis and determination unit, for analyzing the audio frequency signal to determine statuses of components of the semiconductor equipment.

11. The apparatus of claim 10, wherein the analysis and determination unit analyzes the audio frequency signal by utilizing a mel-scale frequency cepstral analysis to determine the statuses of the components of the semiconductor equipment.

12. The apparatus of claim 10, wherein the audio frequency signal receiving unit further analyzes the audio frequency signal to generate an audio frequency data; and compares the audio frequency data with a plurality of reference audio frequency data of an audio frequency characteristics database to determine the statuses of the components of the semiconductor equipment.

13. The apparatus of claim 12, wherein the analysis and determination unit receives a plurality of reference audio frequency signals generated from the semiconductor equipment while the semiconductor equipment is working and the components of the semiconductor equipment are at a plurality of states, respectively; and the analysis and determination unit analyzes the plurality of reference audio frequency signals to generate a plurality of reference audio frequency signals, and builds the audio frequency characteristics database according to the reference audio frequency signals.

14. The apparatus of claim 13, wherein for each reference audio frequency signal, the analysis and determination unit performs a syllable segmentation operation upon the reference audio frequency signal to generate a plurality of syllables, performs a calculation step upon the plurality of syllables by using mel-frequency cepstrum coefficients to generate a plurality of eigen values, where the plurality of eigen values are designated as an eigen vector, and generates a reference audio frequency data which corresponds to the reference audio frequency signal according to the eigen vector.

15. The apparatus of claim 14, wherein the analysis and determination unit utilizes a linear discrimination analysis to separate the eigen vector and other eigen vectors to generate the reference audio frequency data which correspond to the reference audio frequency signal.

16. The apparatus of claim 10, wherein the analysis and determination unit determines which component of the semiconductor equipment is in an abnormal state and requires replacing.

17. The apparatus of claim 10, wherein the analysis and determination unit determines which component of the semiconductor equipment is in an alarm state and requires maintenance.

18. The apparatus of claim 10, wherein the semiconductor equipment is a coater and developer.

* * * * *